US006242441B1

(12) United States Patent
Kothe et al.

(10) Patent No.: US 6,242,441 B1
(45) Date of Patent: Jun. 5, 2001

(54) USE OF BRINZOLAMIDE TO PREVENT VISUAL FIELD LOSS

(75) Inventors: Angela C. Kothe; Lewis H. Silver, both of Mansfield; Thomas R. Dean, Weatherford, all of TX (US)

(73) Assignee: Alcon Laboratories, Inc., Fort Worth, TX (US)

( * ) Notice: Subject to any disclaimer, the term of this patent is extended or adjusted under 35 U.S.C. 154(b) by 0 days.

(21) Appl. No.: 09/581,687

(22) PCT Filed: Nov. 5, 1998

(86) PCT No.: PCT/US98/23610

§ 371 Date: Jun. 15, 2000

§ 102(e) Date: Jun. 15, 2000

(87) PCT Pub. No.: WO99/32123

PCT Pub. Date: Jul. 1, 1999

Related U.S. Application Data

(60) Provisional application No. 60/068,767, filed on Dec. 23, 1997.

(51) Int. Cl.[7] .................................................. A67K 31/535
(52) U.S. Cl. .................................... 514/222.8; 514/226.5; 514/912
(58) Field of Search ............................. 514/226.5, 222.8, 514/912

(56) References Cited

U.S. PATENT DOCUMENTS

| 5,240,923 | 8/1993 | Dean et al. | 514/226.5 |
|---|---|---|---|
| 5,378,703 | 1/1995 | Dean et al. | 514/222.8 |

OTHER PUBLICATIONS

Crick, et al., "Relationship Between Intraocular Pressure and Visual Field Progress in Chronic Simple Glaucoma and Ocular Hypertension," *Glaucoma,* 7:208–219, 1985.

Sommer, Alfred, "Intraocular Pressure and Glaucoma," *American Journal of Ophthalmology,* vol. 107(2):186–188 Feb. 1989.

Mao, et al., "Correlation Between Intraocular Pressure Control and Progressive Glaucomatous Damage in Primary Open–Angle Glaucoma," *American Journal of Ophthalmology,* vol. 111:51–55, Jan. 1991.

Crichton, et al., "Unequal Intraocular Pressure and Its Relation to Asymmetric Visual Field Defects in Low–Tension Glaucoma," *Ophthalmology,* vol. 96(9):1312–1314, Sep. 1989.

Wegner, et al., "Visual Field Changes After One Year Treatment with Dorzolamide in Patients with Primary Open Angle Glaucoma," *Societé Ophthalmologique Europeénne,* 1997.

Johnson, Chris A., "Standardizing the Measurement of Visual Fields for Clinical Research," *Ophthalmology,* vol. 103(1):186–189, Jan. 1996.

Dean, et al. "Brinzolamide (AL–4862) Suspension is a New Topically Active Carbonic Anhydrase Inhibitor in the Dutch–Belted Rabbit and Cynomolgus Monkey," *Investigative Ophthalmology & Visual Science,* vol. 38(4):S813, Mar. 15, 1997 (Abstract 3786–B387).

C. Camras, "A Triple–Masked Primary Therapy Study of the Efficacy and Safety of BID and TID–Dosed Brinzolamide 1% Compared to TID–Dosed Dorzolamide 2% and BID–Dosed Timolol 0.5%," *Investigative Ophthalmology & Visual Science,* vol. 38(4):S560, Mar. 15, 1997 (Abstract 2606–B296).

Sommer, Alfred, "Glaucoma risk factors observed in the Baltimore Eye Survey," *Current Opinion in Glaucoma,* vol. 7(2):93–98, Apr. 1996.

Sommer, et al., "Relationship Between Intraocular Pressure and Primary Open–Angle Glaucoma Among White and Black Americans," The Baltimore Eye Survey, *Arch Ophthalmology,* vol. 109:1090–1095, Aug. 1991.

Tielsch, et al., "Racial Variations in the Prevalence of Primary Open–angle Glaucoma," The Baltimore Eye Survey, *JAMA,* vol. 266(3):369–374, Jul. 17, 1991.

Tielsch, et al., "Blindness and Visual Impairment in an American Urban Population," The Baltimore Eye Survey, *Arch Ophthalmology,* vol. 108:286–290, Feb. 1990.

Dielemans, et al., "The Prevalence of Primary Open–angle Glaucoma in a Population–based Study in the Netherlands," The Rotterdam Study, *Ophthalmology,* vol. 101(11):1851–1855, Nov. 1994.

Leske, et al., "Risk Factors for Open–angle Glaucoma," The Barbados Eye Study, *Arch Ophthalmology,* vol. 113:918–924, Jul. 1995.

*Primary Examiner*—Zohreh Fay
(74) *Attorney, Agent, or Firm*—Sally S. Yeager

(57) ABSTRACT

Methods for preventing or slowing visual field loss are disclosed.

4 Claims, No Drawings

USE OF BRINZOLAMIDE TO PREVENT VISUAL FIELD LOSS

This application claims the benefit of Provisional application Ser. No. 60/068,767, filed Dec. 23, 1997.

The present invention is directed to the topical use of brinzolamide to prevent visual field loss.

BACKGROUND OF THE INVENTION

While not the sole risk factor, elevated intraocular pressure is the major risk factor for the development of glaucomatous optic neuropathy. The relationship between intraocular pressure (IOP) and glaucoma is such that the risk of having or developing glaucomatous optic neuropathy, or suffering progressive damage while receiving medical therapy or following surgical treatment is directly related to the level of intraocular pressure. See, Crick, et al., *Glaucoma*, 7:208–219 (1995); Sommer, *American Journal of Ophthalmology*, Vol. 7, No. 2 (February, 1989); and Mao, et al., *American Journal of Ophthalmology*, Vol. 111, No. 1 (January, 1991). Additionally, a correlation exists between asymmetric damage and asymmetric IOP, Crichton, et al., *Ophthalmology*, Vol. 96, No. 9, (September, 1989), with the greater amount of damage observed in the eye with the higher IOP. Epidemiological surveys, such as the Baltimore Eye Survey, the Rotterdam Study, and the Barbados Eye Study have also demonstrated an increased prevalence of primary open-angle glaucoma associated with increasing IOP.

Wegner et al. (Societe Ophtalmologique Europeenne, 1997) assessed the effect of dorzolamide (a 2% topical carbonic anhydrase inhibitor) on the visual fields of patients with primary open-angle glaucoma (POAG) following one year of treatment. Visual fields were assessed using Octopus perimetry. Of the 49 patients, 39 required adjunctive IOP-lowering therapy, while only 10 were treated with dorzolamide alone.

The patients treated with dorzolaride alone had an improvement in their visual fields as determined by a decrease in the Octopus Mean Defect from 9.36 dB to 8.26 dB, and an increase in the Mean Sensitivity from 17.72 dB to 18.77 dB. The 39 patients treated with dorzolamide plus adjunctive therapy also exhibited an improvement in their visual fields as seen by a decrease in the Mean Defect from 8.07 dB to 7.52 dB, and an increase in Mean Sensitivity from 18.51 dB to 18.96 dB. Changes were reported to be significant ($p<0.01$).

Brinzolamide is disclosed in commonly assigned U.S. Pat. Nos. 5,240,923 and 5,378,703 for its usefulness in controlling intraocular pressure, particularly in the treatment of glaucoma. These patents are incorporated herein by reference.

SUMMARY OF THE INVENTION

The present invention is directed to the topical use of brinzolamide formulations to prevent or slow visual field loss in persons suffering from ocular hypertension or glaucoma.

DESCRIPTION OF PREFERRED EMBODIMENTS

MD (mean deviation) and CPSD (corrected pattern standard deviation) are global indices provided by the Humphrey Field Analyzer statistical package. CPSD is a measure of how much the total shape of the patient's visual field deviates from that of the age-matched, normative reference field. If the sensitivity gradient is irregular (as occurs in a scotoma due to glaucoma), a higher CPSD will be recorded. Values for CPSD are positive, and approximate zero in a normal visual field. MD is a measure of the average elevation or depression of the patient's overall field compared to the normal reference field. Values for MD are approximately zero in a normal field and can be either positive or negative. Positive values for MD indicate that the patient's overall field is better than that of the normal age-corrected reference field, while negative values indicate that the patient's overall field is worse than that of the normal age-corrected reference field.

Glaucoma is believed to result in areas of localized loss rather than diffuse loss of sensitivity of the visual field. Since MD is unable to differentiate between a deep localized loss (scotoma due to glaucoma) or diffuse widespread loss (resulting from a small pupil size, uncorrected refractive error, development of cataract, etc.), CPSD is more relevant and useful in detecting and tracking early to moderate glaucomatous visual field loss. Once field loss has reached a significant level of severity (CPSD>10 dB and MD<−25 dB) analysis of the CPSD is no longer useful since with increased severity of loss, the localized nature of the loss is diminished.

The Eye Care Technology Forum has specifically recommended that for studies of glaucoma and ocular hypertension (OHT), analysis procedures be based on localized changes, such as are indicated by the CPSD. See, Johnson, *Ophthalmology*, Vol. 103, No. 1 (January, 1996).

It has been surprisingly found that brinzolamide, (R-(+)-4-ethylamino-3,4-dihydro-2-(3-methoxy)propyl-2H-thieno[3,2,e]1,2-thiazine-6-sulfonamide-1,1-dioxide), is equally effective as timolol in maintaining the visual field in patients with primary open angle glaucoma or ocular hypertension. The results are surprising in view of the superior IOP lowering efficacy of the beta-blocker, timolol, versus brinzolamide and the relationship between elevated IOP and glaucoma previously discussed. (Brinzolamide reduces elevated IOP from 15–19% while timolol reduces elevated IOP from 22–26%.)

The following represents a summary of the visual field data observed in a long-term study comparing the efficacy of BID- and TID-dosing with brinzolamide versus BID-dosing with timolol.

Data were analyzed as a function of patients diagnosed with POAG or OHT, as well as only those with POAG (since, by definition those diagnosed as OHT at the onset of the study, did not exhibit glaucomatous field loss). In addition, patients were sub-classified as to those who received only study medication throughout the 12 month period and those who required adjunctive therapy with another ocular hypotensive agent (miotic, alpha-agonist, sympathomimetic, prostaglandin, etc.). The following shorthand notations are used in the data presentation: Brinzolamide (BZ); Timolol (TIM); delta MD=month 12 MD-month 0 MD; delta CPSD=month 12 CPSD-month 0 CPSD.

| | Patients diagnosed with POAG (n = 144) or OHT (n = 81) | | | | | |
|---|---|---|---|---|---|---|
| | study medication only | | | study medication with or without adjunctive therapy | | |
| Parameter | BZ BID | BZ TID | TIM BID | BZ BID | BZ TID | TIM BID |
| delta MD | −0.38dB | −0.78dB | −0.30dB | −0.28dB | −0.85dB | −0.30dB |
| p value | 0.0745 | 0.0003 | 0.3033 | 0.2006 | 0.0002 | 0.3195 |
| | BZ BID = BID TIM p = 0.8299 | | | BZ BID = BID TIM p = 0.9513 | | |
| | BZ TID = BID TIM p = 0.1892 | | | BZ TID = BID TIM p = 0.1466 | | |
| delta CPSD | −0.03dB | +0.21dB | −0.16dB | +0.09dB | +0.27dB | −0.07dB |
| p value | 0.8795 | 0.2607 | 0.5300 | 0.6262 | 0.1639 | 0.7819 |
| | BZ BID = BID TIM p = 0.6745 | | | BZ BID = BID TIM p = 0.6108 | | |
| | BZ TID = BID TIM p = 0.2418 | | | BZ TID = BID TIM p = 0.2946 | | |
| N | 84 | 83 | 44 | 91 | 87 | 47 |

Note: for the Humphrey perimeter, a negative value for the delta MD indicates worsening and a positive value for the delta MD indicates improvement; a negative value for the delta CPSD indicates improvement and a positive value for the delta CPSD indicates worsening Results demonstrated that BID- or TID-dosing with brinzolamide was statistically and clinically similar in its effect on the visual field (as assessed by MD or CPSD) to BID-dosing with timolol.

| | Only those patients diagnosed with POAG (n = 144) | | | | | |
|---|---|---|---|---|---|---|
| | study medication only | | | study medication with or without adjunctive therapy | | |
| Parameter | BZ BID | BZ TID | TIM BID | BZ BID | BZ TID | TIM BID |
| delta MD | −0.02dB | −0.82dB | −0.39dB | −0.13dB | −0.92dB | −0.38dB |
| p value | 0.9420 | 0.0051 | 0.3384 | 0.6601 | 0.0023 | 0.3627 |
| | BZ BID = BID TIM p = 0.4099 | | | BZ BID = BID TIM p = 0.3187 | | |
| | BZ TID = BID TIM p = 0.3844 | | | BZ TID = BID TIM p = 0.2869 | | |
| delta CPSD | −0.02dB | +0.30dB | −0.18dB | +0.17dB | +0.38dB | −0.03dB |
| p value | 0.9428 | 0.2338 | 0.6096 | 0.5082 | 0.1398 | 0.9232 |
| | BZ BID = BID TIM p = 0.7072 | | | BZ BID = BID TIM p = 0.6483 | | |
| | BZ TID = BID TIM p = 0.2683 | | | BZ TID = BID TIM p = 0.3460 | | |
| N | 52 | 51 | 26 | 59 | 56 | 29 |

Note: for the Humphrey perimeter, a negative value for the delta MD indicates worsening and a positive value for the delta MD indicates improvement; a negative value for the delta CPSD indicates improvement and a positive value for the delta CPSD indicates worsening.

Results demonstrated that BID- or TID-dosing with brinzolamide was statistically and clinically similar in its effect on the visual field (as assessed by MD or CPSD) to BID-dosing with timolol.

Brinzolamide is preferably formulated as a topical ophthalmic suspension with a pH of 4.5–7.8. It will normally be contained in the formulation at a concentration of 0.1%–10% by weight, preferably 0.25%–5.0% by weight. Thus, for topical presentation, one to three drops of these formulations would be delivered to the surface of the eye one to four times a day according to the routine discretion of a skilled clinician.

The following formulation is useful for preventing the visual field loss associated with glaucoma or ocular hypertension.

EXAMPLE

| Ingredient | Percent w/v |
|---|---|
| Brinzolamide | 1.0 |
| Mannitol | 3.3 |
| Carbopol 974P | 0.4 |
| Tyloxapol | 0.025 |
| Disodium EDTA | 0.01 |
| Benzalkonium Chloride | 0.01 + 5% excess |
| Sodium Chloride | 0.25 |
| Sodium Hydroxide/Hydrochloric Acid | pH 7.5 |
| Purified Water | QS 100 |

What is claimed is:

1. A method of preventing or slowing visual field loss associated with glaucoma or ocular hypertension which comprises administering topically to the eye a pharmaceutically effective amount of brinzolamide.

2. A method according to claim 1, wherein the brinzolamide is administered as a suspension.

3. A method according to claim 1 or 2, wherein the brinzolamide concentration is from 0.1 to 10.0 percent by weight.

4. A method according to claim 3, wherein the concentration is from 0.25 to 5.0 percent by weight.

* * * * *